United States Patent
Roger

(10) Patent No.: US 6,210,358 B1
(45) Date of Patent: Apr. 3, 2001

(54) EAR IRRIGATION DEVICE

(75) Inventor: Gregory James Roger, Crows Nest (AU)

(73) Assignee: Cryptych Pty Ltd, Crows Nest (AU)

( * ) Notice: Subject to any disclaimer, the term of this patent is extended or adjusted under 35 U.S.C. 154(b) by 0 days.

(21) Appl. No.: 09/180,527

(22) PCT Filed: May 6, 1997

(86) PCT No.: PCT/AU97/00274

§ 371 Date: Jan. 28, 1999

§ 102(e) Date: Jan. 28, 1999

(87) PCT Pub. No.: WO97/42921

PCT Pub. Date: Nov. 20, 1997

(30) Foreign Application Priority Data

May 9, 1996 (AU) .................................................. PN 9762

(51) Int. Cl.[7] .................................................. A61M 3/00
(52) U.S. Cl. .............................. 604/43; 604/28; 604/275; 604/257; 604/514
(58) Field of Search .............................. 604/310, 54, 290, 604/200, 213, 150, 43, 93.01, 117, 131, 173, 187, 257, 275, 276, 317, 911; 600/559, 200

(56) References Cited

U.S. PATENT DOCUMENTS

| | | |
|---|---|---|
| 4,036,235 | 7/1977 | Hathaway ............................ 128/292 |
| 4,106,493 | 8/1978 | Proctor et al. ............................ 128/2 |
| 4,201,212 | 5/1980 | Bradley ................................ 128/275 |
| 4,206,756 | 6/1980 | Grossan ............................... 128/229 |
| 4,244,377 | 1/1981 | Grams ................................. 128/742 |
| 4,258,714 | 3/1981 | Leopoldi et al. ..................... 128/232 |
| 4,804,362 | 2/1989 | Enzo ........................................ 604/1 |
| 5,309,899 | 5/1994 | Ginsberg ............................... 604/38 |
| 5,364,343 | 11/1994 | Apolet et al. .......................... 604/43 |
| 5,395,357 | 3/1995 | Weigel ................................. 604/346 |
| 5,944,711 | * 8/1999 | Pender ................................. 604/514 |

FOREIGN PATENT DOCUMENTS

| | | |
|---|---|---|
| 0243261 | 10/1987 | (EP) . |
| 0502485 | 9/1992 | (EP) . |
| 2185688 | 7/1987 | (GB) . |
| WO84/02655 | 7/1984 | (WO) . |
| WO96/14098 | 5/1996 | (WO) . |

* cited by examiner

Primary Examiner—Glenn K. Dawson
(74) Attorney, Agent, or Firm—Jacobson, Price, Holman & Stern, PLLC

(57) ABSTRACT

An earpiece for cleaning wax or other foreign material from the ear canal of a patient or delivering a therapeutic agent into the ear canal. The device has a fluid outlet that directs the fluid passing therethrough at an oblique angle to the longitudinal axis of the device. The fluid is thereby directed at the wall of the ear canal so reducing the likelihood of damage to the delicate structures of the eardrum. The device is also designed to allow inspection of the ear canal when it is in place so removing the need of repositioning equipment following cleaning of the canal.

20 Claims, 1 Drawing Sheet

EAR IRRIGATION DEVICE

FIELD OF THE INVENTION

The present invention relates to an earpiece that can be used for cleaning wax and other matter from the ear canal of a patient and in particular the external auditory canal.

BACKGROUND OF THE INVENTION

Accumulation of wax in the external auditory canal can cause reduced hearing, tinnitus (ie. ringing in the ears) and some discomfort, as well as predisposing the ear to infection.

The current typical practice for removing the build-up of ear wax involves the introduction of a cleaning fluid, such as water, into the canal using a syringe. The introduced fluid circulates in the canal and then drains out of the ear carrying with it the wax and any other foreign matter present in the canal. The fluid, wax and/or foreign matter draining from the ear is typically collected in a dish or other vessel which is held below the ear.

Some problems with the current method are that it is messy, not very effective and that there is a high incidence of perforation of the eardrum. This latter problem results from the injected fluid or in some instances the syringe being introduced too far into the canal and inadvertently directly striking the delicate structures of the eardrum.

It would be desirable to have an apparatus for cleaning wax and other foreign matter from the ear canal which presented a decreased risk of damaging the eardrum.

SUMMARY OF THE INVENTION

According to a first aspect, the present invention comprises an earpiece having a longitudinal axis and arranged to allow at least partial visualisation of an ear canal when the earpiece is in the ear canal, the earpiece having a fluid outlet through which fluid may be directed into the ear canal and which is adapted to direct the fluid passing through the outlet at an oblique angle to the longitudinal axis and against the surface of an ear canal into which the earpiece has been introduced.

The earpiece can be used to direct a cleaning fluid into the ear canal to clean wax and other matter therefrom while allowing simultaneous visualisation of the canal. The earpiece can also be used to deliver a therapeutic agent, such as ear drops, into the ear canal.

A fluid delivery means is preferably connected to the fluid outlet of the earpiece. The delivery means can comprise a tube having one end connected to the fluid outlet of the earpiece. The tube can be integral with the earpiece. The other end of the tube can be connected to any suitable fluid supply means. The fluid supply means can comprise a tap, bag or syringe and the fluid will typically be water or a therapeutic agent as requirements dictate. The diameter of the tube is preferably kept relatively small to eliminate high pressure jets of water entering the ear canal and so damaging the eardrum.

The earpiece can be fabricated in one piece. The earpiece preferably has a first portion arranged to at least partially enter the ear canal and a second ear abutment portion. The first portion preferably tapers from a first end to a second distal end arranged to be disposed within the ear canal, The taper of the first portion is arranged such that one may still view the ear canal when the first portion is disposed in the ear canal.

The fluid outlet is preferably disposed proximate the distal end of the first portion and can comprise an orifice in the wall of the first portion.

The second ear abutment portion can comprise a cylindrical ring or tapering member of larger diameter than the first portion. The second portion preferably partially overlaps the first end of the first portion. This sets a maximum distance that the first portion may enter the ear canal so reducing the likelihood of damage to the eardrum by insertion of the irrigation device into the ear. The outer end of the second portion preferably has a standard fitting to allow its connection to an auroscope or like device. Either between or during flushing of the ear canal, the auroscope can be mounted to the earpiece so allowing the physician an opportunity to view whether cleaning of the canal or application of the therapeutic agent is complete.

The second portion can also act as a drain for fluid leaving the ear. The second portion preferably has an outlet port through which the fluid and entrained wax or other matter may drain or be suctioned from the ear.

The first and second portions of the earpiece are preferably joined by a plurality of ribs that extend from proximate the first end of the first portion to the overlying second portion.

The earpiece is preferably fabricated from a plastics material, silicone or a combination thereof and can be disposable.

According to a further aspect, the present invention comprises a method for cleaning wax and other matter from an ear canal comprising the steps of inserting the earpiece as defined herein into the ear canal, and directing fluid through the fluid outlet and into the ear canal.

According to a still further aspect, the present invention comprises a method for delivering a quantity of a therapeutic agent in the form of a fluid into all ear canal comprising the steps of inserting the earpiece as defined herein into the ear canal, and directing fluid through the fluid outlet and into the ear canal.

Either of the further aspects can also include the step of visualising the ear canal before, during and/or after the step of directing the fluid through the fluid outlet.

BRIEF DESCRIPTION OF THE DRAWINGS

Hereinafter by way of example only, preferred embodiments of the invention are described with reference to the accompanying drawings, in which.

PREFERRED MODE OF CARRYING OUT THE INVENTION

Figure 1:
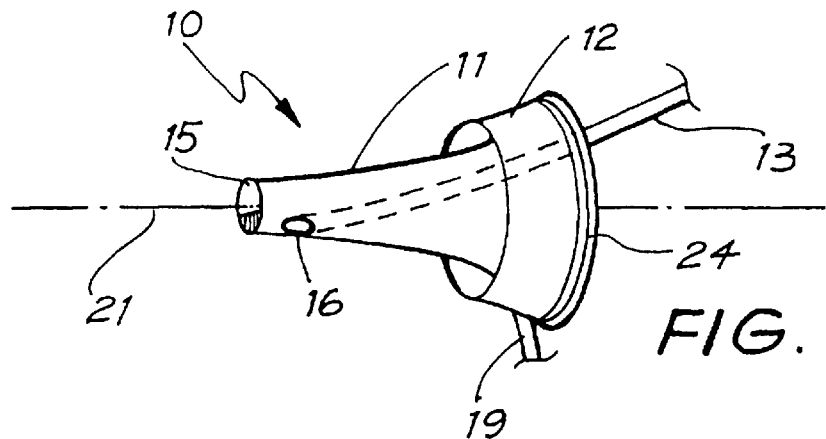
FIG. 1 is a perspective view of one embodiment of an earpiece according to the present invention.

An earpiece for use as an irrigation device or for the delivery of a therapeutic agent, such as ear drops, according to the present invention is generally depicted as 10 in the drawings.

The earpiece 10 comprises a first portion 11, an ear abutment portion 12 and a fluid delivery tube 13.

The first portion 11 tapers from a first end 14 to a truncated inner end 15. A diameter of the inner end 15 is such that the ear canal can still be visualised when the earpiece 10 is placed in the ear canal.

Figures 2, 3:
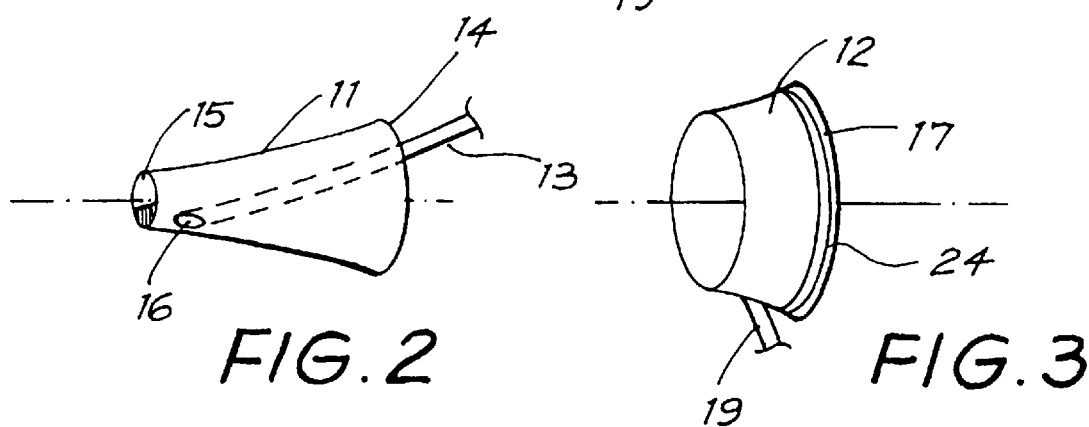
FIG. 2 is a perspective view of the first portion of the earpiece of FIG. 1.
FIG. 3 is a perspective view of the second portion of the earpiece of FIG. 1.

Proximate the inner end 15 is an outlet 16 to which is connected the tube 13 (partially depicted in phantom in FIGS. 1 and 2). The outlet 16 is disposed at an oblique angle to the longitudinal axis 21 of the earpiece 10 such that fluid entering the ear canal firstly strikes and then spirals along the wall surfaces of the ear canal before reaching the eardrum. The other end of the tube is removably connected to a fluid supply means such as a syringe. bag or tap. The small diameter of the tube 13 serves to minimise the maximum pressure of the fluid entering the ear canal so further reducing the risk to the eardrum.

Figure 4:
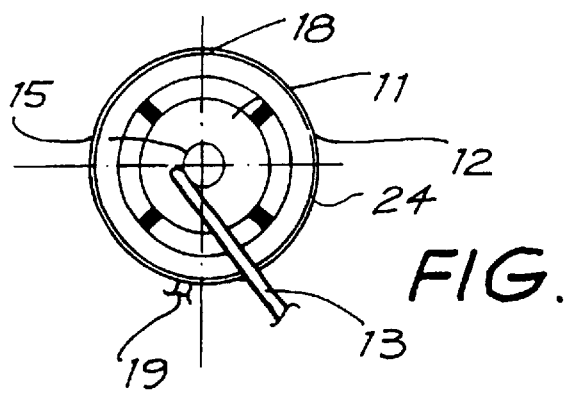
FIG. 4 is an end view of the earpiece of FIG. 1.

Disposed around the first end 14 of the first portion 11 is the second portion 12 of the earpiece 10. The second portion 12 is tapered with its outer 10 end 17 being adapted to connect to an auroscope or like device via a connection means 24. The second portion 12 is connected to the first portion by four ribs 18 best depicted in FIG. 4. Disposed in the wall of the second portion is an outlet port 19 through which fluid and entrained wax or other matter may be drained from the ear to a waste storage means for later disposal.

In use, the earpiece 10 with tube 13 in place will be placed in a patient's ear with the second portion 12 in abutment with the outer surfaces of the ear. The fluid supply is then connected to the tube 13 and is directed into the ear canal through the tube 13. The position of the outlet 16 serves to direct the fluid into and spirally along the wall of the ear canal. This action is useful for cleaning the ear canal as it removes the wax or other matter disposed in the canal. It also allows for the precise delivery of ear drops into ear canal where desired. The motion of the fluid along the wall surfaces of the ear canal also reduces the risk of perforation of the eardrum which can potentially arise from the introduction of a fluid jet entering the ear canal.

The fluid with any entrained wax or matter or excess ear drops can exit the ear through the second portion 12 and out the outlet port 19.

An auroscope can be readily mounted to the outer end 17 of the second portion 12 so allowing visualisation of the ear canal either during or after injection of the fluid into the ear canal.

The arrangement of the earpiece 10 serves to allow cleaning of the ear canal or the placement of ear drops and visualisation of the ear canal without the necessity of repositioning the earpiece 10 following inspection of the ear canal.

Figure 5:
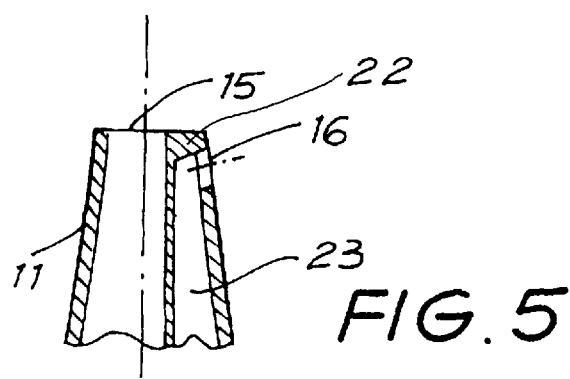
FIG. 5 is an enlarged cross-sectional view of an alternative embodiment of the distal end of the first portion of the earpiece.

FIG. 5 depicts an alternative arrangement for the region proximate the inner end 15 of the first portion 11. In this embodiment, a lumen 23 is formed integrally in the first portion 11 with the outlet 16 being disposed adjacent the inner end 15. In use, fluid can be directed down the lumen 23 where it strikes the end wall 22 and is directed out through the outlet 16 and into the ear canal.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. An earpiece for releasable attachment to an auriscope to allow at least partial visualization of an ear canal when the earpiece is in the ear canal, the earpiece having
    a longitudinal axis,
    a first portion arranged to at least partially enter the ear canal and contact a surface of the ear canal,
    a second ear abutment portion, the second ear abutment portion comprises a member of larger diameter than the first portion,
    the second ear abutment portion only partially overlaping a first end of the first portion so setting a maximum distance that the first portion may enter the ear canal by the second ear abutment portion abutting the ear during insertion of the first portion into the ear canal and thereby reducing the likelihood of damage to the eardrum by insertion of the first portion into the ear,
    said second ear abutment portion including connection means adapted to provide connection of the earpiece to an auriscope, and
    said first portion including a fluid outlet through which fluid may be directed into the ear canal and which is adapted to direct the fluid passing through the outlet at an oblique angle to the longitudinal axis and against a surface of an ear canal into which the earpiece has been introduced.

2. The earpiece of claim 1 wherein a fluid delivery means is connected to the fluid outlet of the earpiece.

3. The earpiece of claim 2 wherein the fluid delivery means comprises a tube having one end connected to the fluid outlet of the earpiece.

4. The earpiece of claim 3 wherein the other end of the tube is connected to a suitable fluid supply means.

5. The earpiece of claim 4 wherein the fluid outlet comprises an orifice in the earpiece adjacent one end of the earpiece.

6. The earpiece of claim 4 wherein the fluid supply means is a tap, bag or syringe.

7. The earpiece of claim 1 wherein the earpiece has a lumen formed integrally therein, the fluid outlet being disposed to allow fluid passing through the lumen to exit the lumen.

8. The earpiece of claim 7 wherein the lumen is connected to a suitable fluid supply means.

9. The earpiece of claim 1 wherein the fluid is water or a therapeutic agent.

10. The earpiece of claim 1 wherein the earpiece is comprised of one piece.

11. The earpiece of claim 1, wherein the first portion tapers from the first end to a second distal end arranged to be disposed within the ear canal.

12. The earpiece of claim 11 wherein the taper of the first portion is arranged such that a user may still view the ear canal when the first portion is disposed in the ear canal.

13. The earpiece of claim 1 wherein the second portion acts as a drain for fluid leaving the ear.

14. The earpiece of claim 13 wherein the second portion has an outlet port through which the fluid and entrained wax or other foreign matter may drain or be suctioned from the ear.

15. The earpiece of claim 1 wherein the earpiece is fabricated from a plastics material.

16. A method for cleaning wax and other matter from an ear canal comprising the steps of inserting the earpiece of claim 1 into the ear canal, and directing fluid through the fluid outlet and into the ear canal.

17. The method of claim 16 further comprising the step of visualising the ear canal before, during and/or after the step of directing the fluid through the fluid outlet.

18. A method for delivering a quantity of a therapeutic agent in the form of a fluid into an ear canal comprising the steps of inserting the earpiece of claim 1 into the ear canal, and directing fluid through the fluid outlet and into the ear canal.

19. An earpiece for releasable attachment to an auriscope to allow at least partial visualization of an ear canal when the earpiece is in the ear canal, the earpiece having a longitudinal axis, a first portion arranged to at least partially enter the ear canal and contact a surface of the ear canal, a second ear abutment portion which only partially overlies a first end of the first portion, the first and second portions of the earpiece are joined by a plurality of ribs that extend from proximate the first end of the first portion to the overlying second portion, connection means on the ear abutment portion, adapted to provide connection of the earpiece to an auriscope, and a fluid outlet through which fluid may be directed into the ear canal and which is adapted to direct the fluid passing through the outlet at an oblique angle to the longitudinal axis and against a surface of the ear canal into which the earpiece has been introduced.

20. An earpiece for releasable attachment to an auriscope to allow at least partial visualization of an ear canal when the earpiece is in the ear canal, the earpiece having a longitudinal axis, a first portion arranged to at least partially enter the ear canal and contact a surface of the ear canal, a second ear abutment portion only partially overlapping a first end of the first portion, the first and second portions of the earpiece are joined by a plurality of ribs that extend from proximate the first end of the first portion to the second portion, connection means on the ear abutment portion, adapted to provide connection of the earpiece to an auriscope, and a fluid outlet through which fluid may be directed into the ear canal and which is adapted to direct the fluid passing through the outlet at an oblique angle to the longitudinal axis and against a surface of the ear canal into which the earpiece has been introduced.

* * * * *